(12) United States Patent
Herrmann

(10) Patent No.: US 10,549,568 B2
(45) Date of Patent: Feb. 4, 2020

(54) MAILER FOR OBTAINING AND TRANSPORTING BIOLOGICAL SAMPLES SUCH AS DNA

(71) Applicant: XEROX CORPORATION, Norwalk, CT (US)

(72) Inventor: Douglas K Herrmann, Webster, NY (US)

(73) Assignee: XEROX CORPORATION, Norwalk, CT (US)

( * ) Notice: Subject to any disclaimer, the term of this patent is extended or adjusted under 35 U.S.C. 154(b) by 0 days.

(21) Appl. No.: 16/143,911

(22) Filed: Sep. 27, 2018

(65) Prior Publication Data

US 2019/0100049 A1   Apr. 4, 2019

Related U.S. Application Data

(60) Provisional application No. 62/565,267, filed on Sep. 29, 2017.

(51) Int. Cl.

| | |
|---|---|
| *B42D 5/02* | (2006.01) |
| *G01N 33/50* | (2006.01) |
| *B01L 3/00* | (2006.01) |
| *A61B 10/00* | (2006.01) |
| *A61B 90/90* | (2016.01) |
| *A61B 90/96* | (2016.01) |
| *B42D 15/08* | (2006.01) |
| *A61B 90/98* | (2016.01) |
| *G01N 1/02* | (2006.01) |

(52) U.S. Cl.
CPC .......... *B42D 5/025* (2013.01); *A61B 10/0045* (2013.01); *A61B 10/0051* (2013.01); *A61B 90/90* (2016.02); *A61B 90/96* (2016.02); *A61B 90/98* (2016.02); *B01L 3/5029* (2013.01); *B01L 3/5055* (2013.01); *B42D 15/08* (2013.01); *G01N 33/5091* (2013.01); *B01L 2200/185* (2013.01); *B01L 2300/069* (2013.01); *G01N 2001/028* (2013.01)

(58) Field of Classification Search
CPC ......... B42D 5/025; A61B 90/90; A61B 90/96; A61B 90/98; A61B 10/0045; A61B 10/0051; B01L 3/5029; B01L 3/5055; B01L 2200/185; G01N 33/5091
USPC ................ 229/68.1, 92.8, 921; 206/223, 569
See application file for complete search history.

(56) References Cited

U.S. PATENT DOCUMENTS

| | | | | |
|---|---|---|---|---|
| 5,611,433 A | * | 3/1997 | Levy .................. | A61B 10/0096 206/569 |
| 6,866,184 B2 | * | 3/2005 | Wood .................... | B65D 27/04 229/71 |
| 8,568,029 B2 | * | 10/2013 | Kannankeril ........ | B31D 5/0073 206/522 |

(Continued)

*Primary Examiner* — Christopher R Demeree
(74) *Attorney, Agent, or Firm* — Jones Robb, PLLC

(57) ABSTRACT

A mailer for biological samples comprises a substrate, the substrate being foldable into a main panel and a cover panel. The main panel has formed therein at least one swab member, the swab member suitable, in size, shape, and rigidity, to act as a swab for obtaining a biological sample. The swab member is foldable relative to the main panel so the tip of the swab member protrudes from an edge of the main panel and an edge of the cover panel folded over the main panel. A machine-readable code or an electronic device is disposed on the swab member.

20 Claims, 4 Drawing Sheets

(56) References Cited

U.S. PATENT DOCUMENTS

| | | | |
|---|---|---|---|
| 2009/0291449 A1* | 11/2009 | Knapp, Jr. | A61B 10/0096 |
| | | | 435/6.11 |
| 2013/0247694 A1* | 9/2013 | Chen | G01N 1/10 |
| | | | 73/864 |
| 2015/0297196 A1* | 10/2015 | Ching | A61B 10/0045 |
| | | | 206/223 |
| 2017/0246625 A1* | 8/2017 | Becker | B01L 3/502 |

* cited by examiner

MAILER FOR OBTAINING AND TRANSPORTING BIOLOGICAL SAMPLES SUCH AS DNA

REFERENCE TO PROVISIONAL APPLICATION

The present Application claims priority from U.S. Provisional Application Ser. No. 62/565,267, filed Sep. 29, 2017.

TECHNICAL FIELD

The present Disclosure relates to a "mailer," i.e., a package suitable for obtaining and transporting a biological sample, such as a sample of DNA from a mouth or other bodily area of a human or other organism.

BACKGROUND

There is a need for a low-cost, easy-to-manufacture package useful for obtaining and transporting biological samples, in particular, DNA obtained from mouth-swabs of humans or animals. It is desirable that the package be easily used by a relatively unskilled human in obtaining the sample, from himself or another human; enclosing the sample to avoid contamination; and transporting the sample in the package through, for example, the public postal system, or by use of a drone. Such a package can be referred to as a "mailer."

SUMMARY

A mailer for biological samples comprises a substrate, the substrate being foldable into a main panel and a cover panel. The main panel has formed therein at least one swab member, the swab member suitable, in size, shape, and rigidity, to act as a swab for obtaining a biological sample. The swab member is foldable relative to the main panel so the tip of the swab member protrudes from an edge of the main panel and an edge of the cover panel folded over the main panel. A recording entity, such as a machine-readable code, is provided on the swab member.

DESCRIPTION

FIGS. 1-4 are a series of perspective views of different embodiments of a mailer. In each embodiment, the mailer is largely formed from a single substrate generally indicated as 10. This substrate comprises a material suitable for being printed upon and folded; for example, card stock or plastic. The substrate 10 can be pre-formed with thin or scored areas conducive to folding, or can simply be folded as part of a manufacturing process. The substrate 10 is of a typical size that it could be held easily in one hand, like a sheet from an office printer.

As shown in each FIGS. 1-4, the substrate 10 is folded into distinct panels. Taking first the FIG. 1 embodiment, the substrate 10 is folded into a main panel 20 and a cover panel 22. Further, the main panel 20 has formed therein two swab members, indicated as 30 and 32. Each swab member, in one embodiment, is formed by a die-cut in the main panel 20.

Each swab member 30, 32 is suitable, in terms of size, shape, and rigidity, to act as a swab for obtaining a biological sample for a given purpose, such as scraping a DNA sample from the inside of a human cheek.

Figure 1:
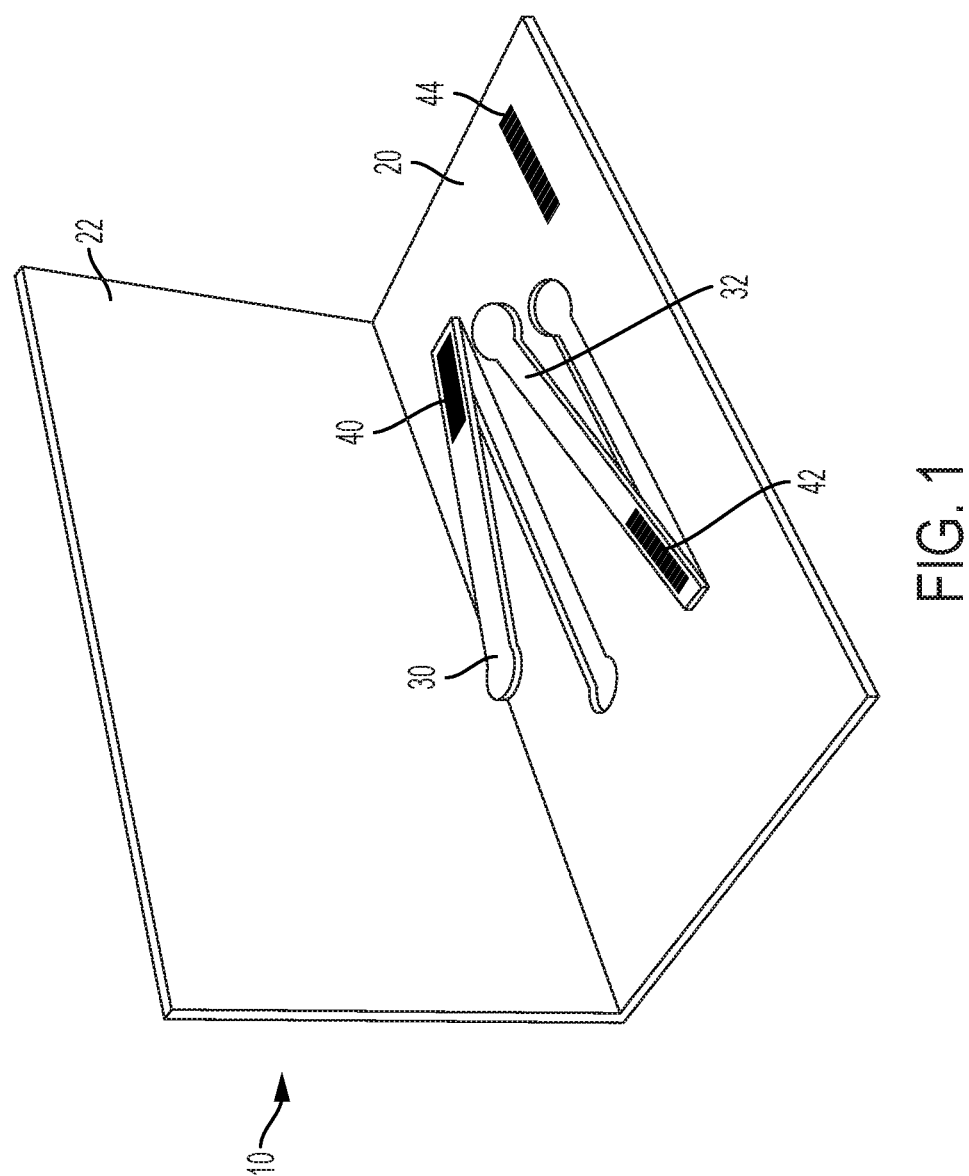
FIGS. 1-4 are a series of perspective views of different embodiments of a mailer.

As shown in FIG. 1, each swab member 30, 32 is configured with one "bridge" to the rest of panel 20, so that the swab member can be folded away (such as 180 degrees) from the rest of main panel 20 while remaining attached to the main panel 20, and also so the swab member can be folded back into its original position. Depending on the material of substrate 10, there may be scoring or other intentionally-provided weakness at the intended fold axis.

As shown in FIG. 1, the swab members 30, 32 are arranged parallel to each other. When the swab members 30, 32 are folded 180 degrees and the cover panel 22 is folded over main panel 20, the end or tips of the swab members 30, 32 protrude from the edge of the panels 20, 22. In the FIG. 1 embodiment, the swab members 30, 32 fold away from the main panel 20 in opposite directions; in other possible embodiments, the swab members can be arranged to fold in the same direction, or at an angle, such as 90 degrees, from each other. In alternate embodiments, there may be provided any number of swab members, and different swab members may be oriented to fold in different directions. Different swab members on the same panel 20 may be formed with different dimensions or shapes, for instance, to provide swabbing of different types or of different body areas.

Also as seen in FIG. 1, there is provided on specific areas of the mailer "recording entities," such as barcodes 40, 42, 44. Although barcodes are shown, any type of machine-readable code will be suitable for a given application and workflow. Barcode 40 is printed on the stalk of swab member 30 and barcode 42 is printed on the stalk of swab member 32. In a laboratory workflow, it is desirable that the barcode such as 40 is placed near enough a tip (or other likely biological-material bearing surface) on swab member 30, so that, if the swab member such as 30 is removed or separated from main panel 20 (such as to be placed in another machine), the barcode 40 is likely to go with the tip of swab member 30. It is further desirable to have a barcode 44 on the main panel 20 itself, in case it is needed to track a removed tip such as 30 relative to an incoming mailer at a laboratory.

Figure 2:
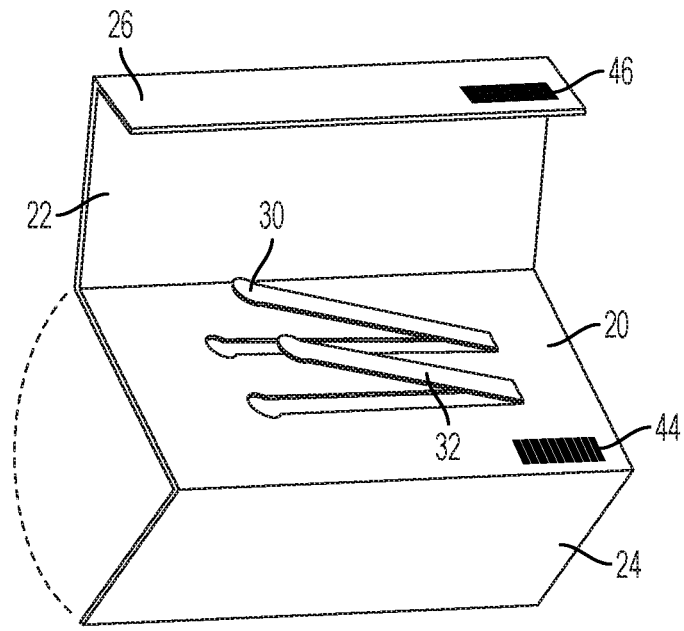

FIG. 2 shows an alternative embodiment of a mailer. In addition to the elements shown and described with FIG. 1, there is provided a backing panel 24, attached to main panel 20, and a flap panel 26, attached to cover panel 22. The backing panel 24 is attached by adhesive to the rear side of main panel 20 as shown in the Figure. (The backing panel 24 is not shown attached to the rear side of main panel 20 in the Figure, but its folding relationship with main panel 20 is apparent.) When the backing panel 24 is so attached, closing of the cover panel 22 over the front side of main panel 20 will cause a double-sided enclosure of the swab members 30, 32. There is further provided a flap panel 26, which may include some kind of adhesive (tear strip, moist-enable glue, etc.) associated therewith. After the biological sample has been taken and is attached to the tips of swab members 30, 32, the swab members 30, 32 can be folded to their original positions flush with the body of main panel 20, and then covered with cover panel 22, cover panel 22 can then be sealed with flap panel 26. In combination with backing panel 24, the biological sample is reasonably sealed for mailing in the mailer. There may further be provided external bar codes such as 46 or other information, such as shipping addresses or postal codes, anywhere on an external surface of the folded mailer to enable the mailer to be placed directly in a physical mail system.

Figure 3:
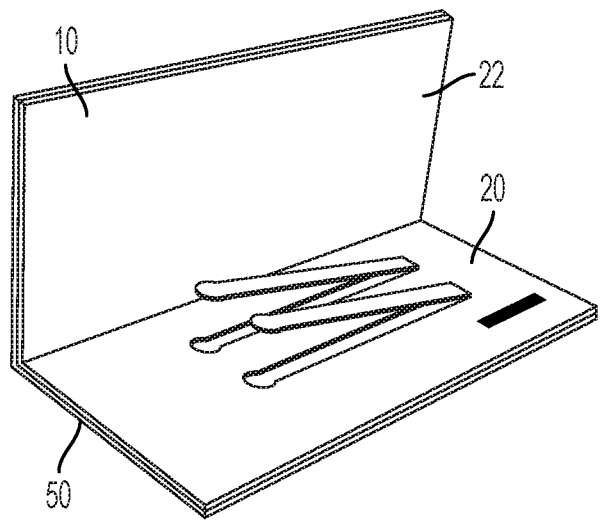

FIG. 3 shows an alternative embodiment of a mailer. In addition to the elements shown and described with FIG. 1, there is provided a lamination layer 50. This lamination layer likely comprises a moisture-proof material such as plastic. The lamination layer 50 may be attached only to the main panel 20, or any or all panels of a substrate 10, as shown. The lamination layer 50, in one embodiment, forms a non-permeable outer coating to protect the obtained DNA or other material from external exposure.

Figure 4:
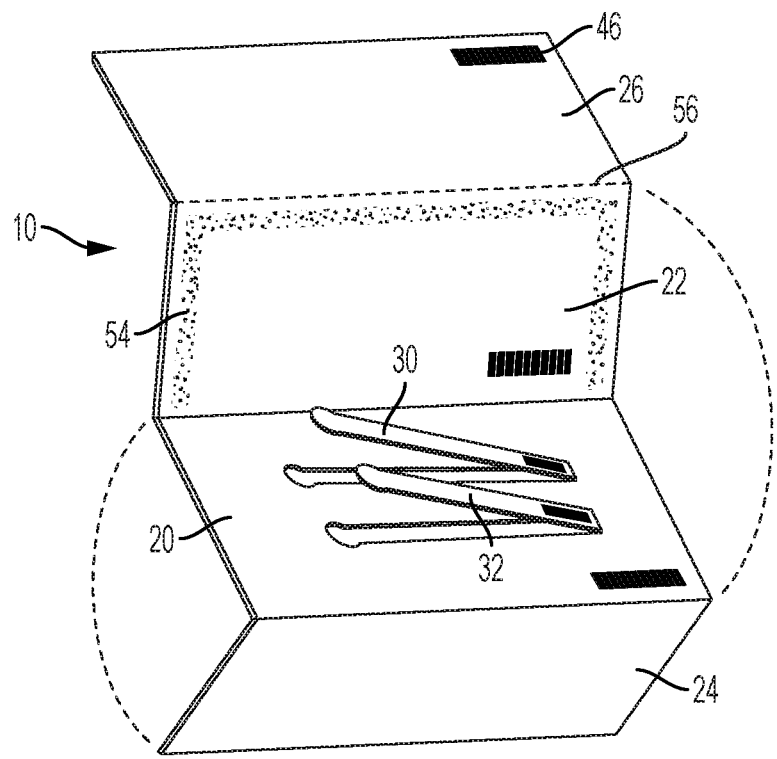

FIG. 4 shows an alternative embodiment of a mailer. In addition to the elements shown and described with FIGS. 1 and 2, there is provided a quantity of adhesive 54 around the periphery of cover panel 22, so that, when cover panel 22 is closed over main panel 20, the adhesive 54 provides a robust enclosure around the tips of swab members 30, 32. The adhesive 54 can be made active by use of a tear strip (not shown). Also, as shown in the FIG. 4 embodiment, the flap panel 26, which may not be needed to enclose the mailer, can be attached by a perforation 56, for easy removal as a receipt before the mailer is placed in a physical mail system. Such a receipt would include the bar code 46. A tamper resistant adhesive, or tamper-evident material, can be associated with the flap panel 26 to provide an indication of tampering.

Figure 5:
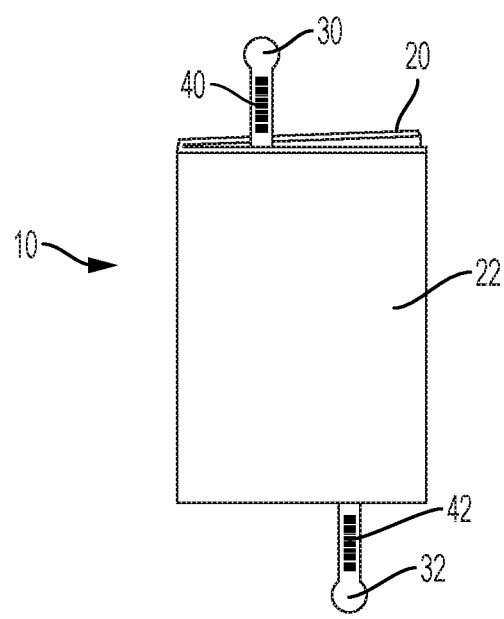
FIG. 5 is a perspective view showing a mailer having portions thereof positioned so that the mailer can be used to obtain, for instance, a DNA sample from a human mouth.

FIG. 5 shows a mailer formed from a substrate 10, of a configuration shown in the FIG. 1 embodiment described above, where the swab members 30, 32 are folded outward and the cover panel 22 is folded over main panel 20. Given typical dimensions of such a mailer, the body of the mailer can be held easily in the hand so a person could scrape DNA samples onto the tips of swab members 30, 32 from his own mouth or the mouth of another. Typically, after the biological sample has been taken and is attached to the tips of swab member 30, 32, the swab members 30, 32 can be folded to their original positions flush with the body of main panel 20, and then covered with cover panel Also shown in FIG. 5 is the positioning of bar codes 40, 42, associated respectively with swabs 30, 32, toward the distal end of each swab so that, when the swabs are folded outward, the bar codes are visible. For various reasons, some having to do with subsequent processing of the swabs such as being cut off from the returned mailer 10, it is desirable to have the barcode as close to the tip of the swab as possible.

Figure 6:
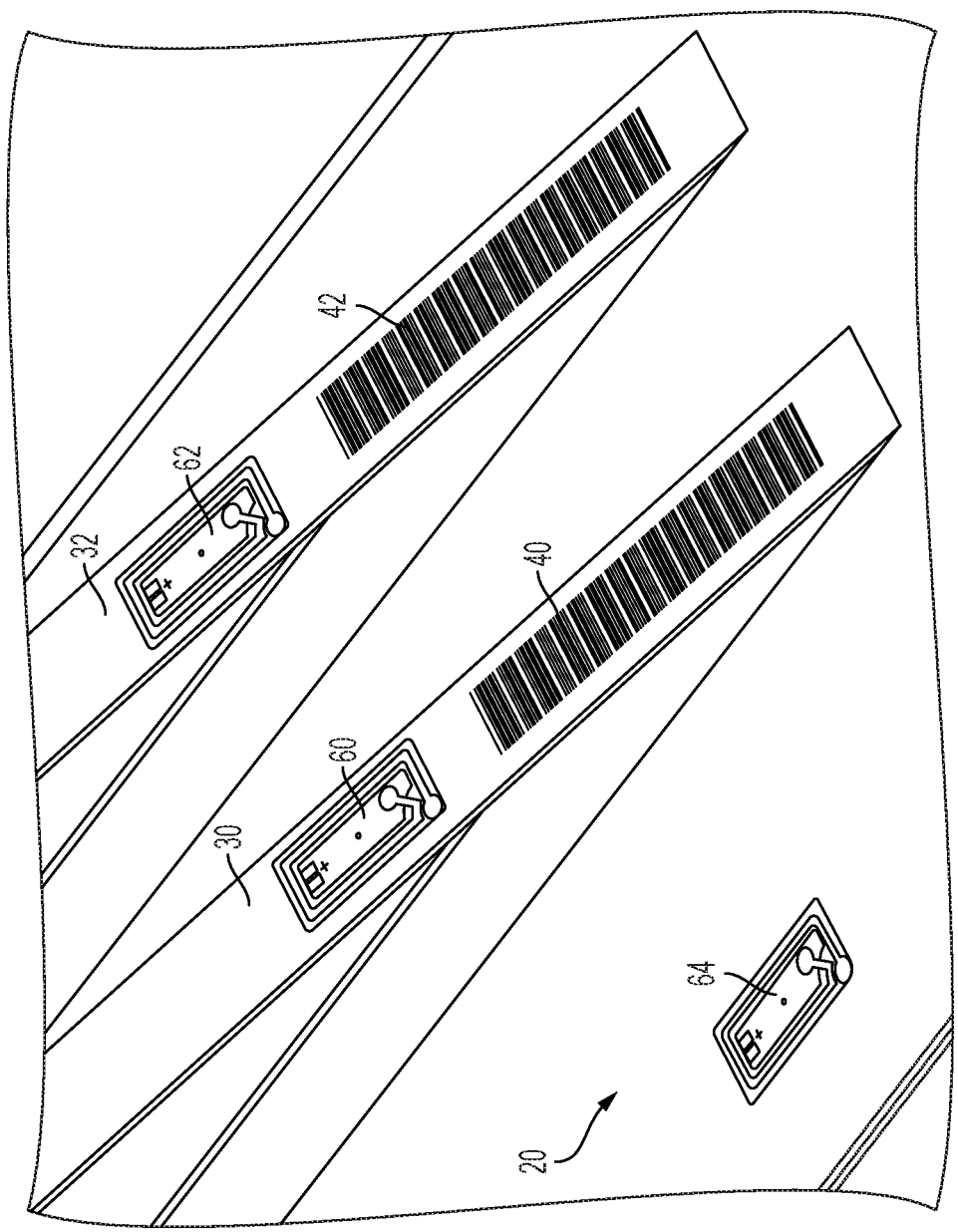
FIG. 6 is detailed perspective view of two swabs folded from a substrate, having electronic devices attached thereto.

In an alternate embodiment, the barcodes 40, 42, 44 as shown and described above can be augmented with or replaced by "recording entities" in the form of electronic devices, such as RFID chips, printed memory devices, or other passive devices. FIG. 6 is detailed perspective view of two swabs 30, 32, folded from a substrate, having respective devices 60, 62, attached thereto. In addition, another device such as 64 can be attached to the body of the mailer 10, such as on main panel 20.

In other embodiments, laser or die perforations can be provided to the tips of swab 30, 32 to improve biological material acquisition, such as to make the swab more absorbent. A chemical could be applied to the swab tips, as part of a printing or pre- or post-printing process, to provide a color change to the swab when wet to indicate when the swab is ready for mailing.

In practical use, mailers such as shown herein can be manufactured with an additional aspect of sterilization. For instance, sterilization of mailers can be performed upstream of the printing process on substrate 10. By conducting the sterilization at the manufacturer of substrates 10, there are many options for different sterilization methods such as use of gamma radiation or ethylene oxide as a sterilant. This ensures a swab such as 30 is sterile prior to packing and shipping to the printing apparatus. The sterilized swab such as 30 can then be sealed, such as by various means as described above, prior to any shipping, printing and post print converting process, thus protecting the swab 30 from contamination while it is being printed and processed for shipment. An end user can then be assured that the swab has not been previously used and is sterilized for use while allowing for a more robust reading and analysis at the processing lab.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A mailer for biological samples, comprising:
a substrate configured to fold into a main panel and a cover panel; and
a swab member formed in the main panel; the swab member being foldable relative to the main panel to move between a first position, in which a tip of the swab member is coverable by the cover panel when folded over the main panel, and a second position, in which the tip of the swab member protrudes from an edge of the main panel and an edge of the cover panel folded over the main panel;
wherein the tip of the swab member is positioned to collect a biological sample when the swab member is in the second position.

2. The mailer of claim 1, the swab member being defined by cuts in the substrate.

3. The mailer of claim 1, further comprising a recording medium disposed on the swab member.

4. The mailer of claim 3, wherein the recording medium comprises an electronic device.

5. The mailer of claim 3, wherein the recording medium is located on the swab member to be visible when the swab member is folded from the main panel and the cover panel is folded over the main panel.

6. The mailer of claim 3, wherein the recording medium comprises a machine-readable code.

7. The mailer of claim 1, further comprising a lamination layer attached to at least the main panel of the substrate.

8. The mailer of claim 7, the lamination layer comprising a moisture-proof material.

9. The mailer of claim 1, further comprising a flap panel attached to the main panel.

10. The mailer of claim 9, the flap panel having adhesive thereon.

11. The mailer of claim 9, the flap panel having a tamper-evident material associated therewith.

12. The mailer of claim 1, further comprising a quantity of adhesive around a periphery of the cover panel, so that, when the cover panel is closed over the main panel, with the swab member in the first position, the adhesive provides an enclosure around the swab member.

13. The mailer of claim 1, wherein the swab member is a first swab member and further comprising a second swab member.

14. The mailer of claim 1, wherein the tip of the swab member is movable 180 degrees between the first position and the second position.

15. The mailer of claim 1, wherein the swab member remains connected to the main panel during movement between the first and second positions.

16. A mailer for biological samples, comprising a substrate, the substrate being foldable into a main panel and a cover panel;

the main panel having formed therein a first swab member and a second swab member, the first swab member suitable to act as a swab for obtaining a biological sample; the first and second swab members being foldable relative to the main panel so a respective tip of each of the first and second swab members protrudes from an edge of the main panel and an edge of the cover panel folded over the main panel; and a recording entity disposed on the first swab member.

17. The mailer of claim 16, the first swab member and the second swab member being foldable in the same direction.

18. The mailer of claim 16, the first swab member and the second swab member being foldable in different directions.

19. The mailer of claim 16, wherein the first and second swab members are parallel to each other prior to folding relative to the main panel.

20. A mailer for biological samples, comprising:
a substrate configured to fold into a main panel and a cover panel; and
a swab member formed by at least one cut in the main panel of the substrate, the swab member being configured to extend outward from a plane of the main panel, while remaining attached to the main panel, to be placed in contact with and collect a biological sample from a source; and
a recording medium disposed on the at least one swab member.

* * * * *